United States Patent [19]
Gelotte

[11] Patent Number: 5,972,967
[45] Date of Patent: *Oct. 26, 1999

[54] COMPOSITIONS FOR INHIBITING PLATELET AGGREGATION

[75] Inventor: Karl M. Gelotte, North Wales, Pa.

[73] Assignee: Merck & Co., Inc., Rahway, N.J.

[*] Notice: This patent is subject to a terminal disclaimer.

[21] Appl. No.: 08/965,922

[22] Filed: Nov. 7, 1997

Related U.S. Application Data

[62] Division of application No. 08/735,878, Oct. 23, 1996, Pat. No. 5,733,919.

[51] Int. Cl.⁶ .................................................. A61K 31/445
[52] U.S. Cl. ............................................................ 514/331
[58] Field of Search ..................................... 514/331, 318, 514/274, 269

[56] References Cited

U.S. PATENT DOCUMENTS 5,292,756   3/1994   Duggan et al. .......................... 514/331

OTHER PUBLICATIONS

"Remington's Pharmaceutical Sciences" 16 Edition, Mack Publishing Company, Easton, PA (1980) pp. 1488–1497.
"Handbook of Pharmaceutical Excipients" 2nd Edition, A. Wade and P. Weller, Eds., The Pharmaceutical Press, London (1994) pp. 123–125, 443–444 and 454–458.

*Primary Examiner*—Phyllis G. Spivack
*Attorney, Agent, or Firm*—Richard S. Parr; Melvin Winokur

[57] ABSTRACT

The invention is a pharmaceutical composition for intravenous administration to a patient comprising a) a pharmaceutically effective amount of 2-S-(n-Butylsulfonylamino)-3-[4-(4-(piperidin-4-yl)butyloxy)phenyl]propionic acid;

b) a pharmaceutically acceptable amount of a citrate buffer effective to provide a pH of between about 5 and 7; and c) a pharmaceutically acceptable amount of a tonicity adjusting agent effective to make the formulation substantially isotonic with the osmotic pressure of the biological system of the patient.

22 Claims, No Drawings

COMPOSITIONS FOR INHIBITING PLATELET AGGREGATION

This is a division of application Ser. No. 08/735,878 filed Oct. 23, 1996, now U.S. Pat. No. 5,733,919.

BACKGROUND OF THE INVENTION

The invention relates to compositions for inhibiting the binding of fibrinogen to blood platelets, and inhibiting the aggregation of blood platelets by binding fibrinogen receptor antagonists to the gp IIb/IIIa fibrinogen receptor site.

Fibrinogen is a glycoprotein present in blood plasma that participates in platelet aggregation and in fibrin formation. Platelets are cell-like anucleated fragments, found in the blood of all mammals, that also participate in blood coagulation. Interaction of fibrinogen with the IIb/IIIa receptor site is known to be essential for normal platelet function.

When a blood vessel is damaged by an injury or other causative factor, platelets adhere to the disrupted subendothelial surface. The adherent platelets subsequently release biologically active constituents and aggregate. Aggregation is initiated by the binding of agonists, such as thrombin, epinephrine, or ADP to specific platelet membrane receptors. Stimulation by agonists results in exposure of latent fibrinogen receptors on the platelet surface, and binding of fibrinogen to the glycoprotein IIb/IIIa receptor complex.

A multitude of compounds or peptide analogs believed to inhibit platelet aggregation by inhibiting binding to a blood platelet by fibrinogen are known. Duggan et al., U.S. Pat. No. 5,292,756, describes sulfonamide fibrinogen receptor antagonists which are useful for preventing and treating diseases caused by thrombus formation. In a hospital setting, where administration of such compounds is desired, administration may include intravenous (bolus or infusion), intraperitoneal, subcutaneous, or intramuscular form, all using forms well known to those of ordinary skill in the pharmaceutical arts. The compounds may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption.

The compositions of the present invention are safe, storage stable intravenous solutions which are particularly useful for delivering platelet aggregation inhibitors to patients in need of such inhibition.

SUMMARY OF THE INVENTION

The invention is a pharmaceutical composition comprising a) a pharmaceutically effective amount of a compound (also referred to herein as the "active ingredient") having the formula

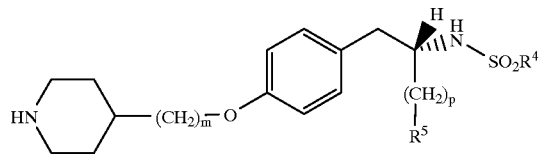

and the pharmaceutically acceptable salts thereof, wherein $R^4$ is aryl, $C_{1-10}$ alkyl, or $C_{1-10}$ arylalkyl;

$R^5$ is

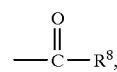

wherein $R^8$ is hydroxy or $C_{1-10}$ alkyloxy;

p is zero or one; and m is an integer from two to six;

b) a pharmaceutically acceptable amount of a citrate buffer effective, e.g. to provide a pH of between about 5 and 7; and c) a pharmaceutically acceptable amount of a tonicity adjusting agent effective to make the formulation substantially isotonic with the osmotic pressure of the biological system of the patient.

The composition is substantially free of phosphate buffer. By "substantially free" is meant that amount of phosphate that provides no pharmaceutically significant pH buffering effect. Such an amount can readily be determined by persons skilled in the art knowing the formulation to be buffered and the pharmaceutically acceptable pH of such formulation.

In one class of compositions, the compositions comprise a pharmaceutically effective amount of a compound having the formula

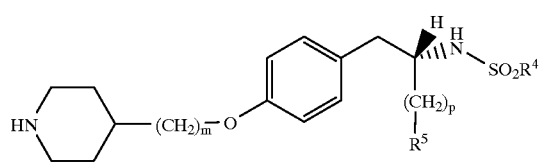

and the pharmaceutically acceptable salts thereof, wherein $R^4$ is aryl, $C_{1-10}$ alkyl, or $C_{1-10}$ arylalkyl;

$R^5$ is

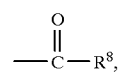

wherein $R^8$ is hydroxy or $C_{1-10}$ alkyloxy;

p is zero or one; and m is an integer from two to six;

an amount of citrate buffer effective to provide a pH of between about 5.8 and 6.2, and about 50–500 milliosmoles of tonicity adjusting agent.

In a subclass of these compositions, the amount of active drug is about 0.01–0.5 mg/ml, the amount of citrate buffer is between about 2 and 100 mM, and the amount of tonicity adjusting agent is between about 50–500 milliosmoles. In a group of this subclass, the amount of citrate buffer is between about 2 and 20 mM, and the amount of tonicity adjusting agent is about 290 milliosmoles. The concentration of active ingredient of the composition represents the amount of anhydrous free base equivalent of the compound present in solution.

In a subgroup of this group, the compound is 2-S-(n-Butylsulfonylamino)-3-[4-(4-(piperidin-4-yl)butyloxy)phenyl]propionic acid.

In a family of this subgroup, the amount of 2-S-(n-Butylsulfonylamino)-3-[4-(4-(piperidin-4-yl)butyloxy)phenyl]propionic acid is about 0.05 to about 0.25 mg/ml, the amount of citrate buffer is about 2–20 mM, and the amount of tonicity adjusting agent is about 290 milliosmoles.

In a specific exemplification of this family, the amount of 2-S-(n-Butylsulfonylamino)-3-[4-(4-(piperidin-4-yl)butyloxy)phenyl]propionic acid is about 0.25 mg/ml, the amount of citrate buffer is about 10 mM, the amount of tonicity adjusting agent is about 290 milliosmoles, and the pH is about 6.

The invention also includes a method for inhibiting the aggregation of blood platelets in a mammal, e.g., a human, comprising intravenously treating the mammal with a pharmaceutically effective amount of the composition of the invention.

In a specific embodiment of this method, the mammal is treated with a composition comprising an amount of 2-S-(n-Butylsulfonylamino)-3-[4-(4-(piperidin-4-yl)butyloxy)phenyl]propionic acid of about 0.25 mg/ml, an amount of citrate buffer of about 10 mM, an amount of tonicity adjusting agent of about 290 milliosmoles, and having a pH of about 6.

DETAILED DESCRIPTION OF THE INVENTION

Formulations of the invention provide enhanced physical and chemical stability to the pharmaceutical compositions. One advantage of such stability is extended pharmaceutical product shelf life. Citrate compositions of the active ingredient are stable for more than 18 months, whereas phosphate formulations of the same active ingredient are not stable. It has been observed, for example, that after 24 months, phosphate formulations contain visible particulates, e.g., those having size greater than 50 μm. Extended pharmaceutical shelf life offers significant economic advantages.

Another advantage of compositions of the invention is enhanced pharmaceutical product safety. Product instability due to extended storage is demonstrated by the formation of insoluble particles that represent potential safety hazards of two types: entry of the insoluble particles into the patient's vein, and clogging of the intravenous in-line filter by the insoluble particles during intravenous administration of the pharmaceutical product. The clarity of intravenous fluids at the time of administration following manipulation in the hospital is an important product attribute. The absence of particulate matter assumes a significant role in view of possible biological hazards resulting from particulate matter.

We have found that compounds of the general formula

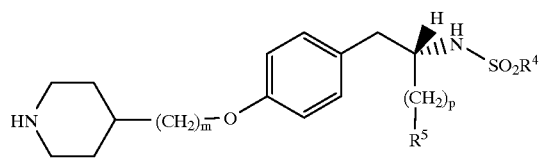

and the pharmaceutically acceptable salts thereof, wherein $R^4$ is aryl, $C_{1-10}$ alkyl, or $C_{1-10}$ arylalkyl;

$R^5$ is

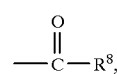

wherein $R^8$ is hydroxy or $C_{1-10}$ alkyloxy;

p is zero or one; and m is an integer from two to six;

exemplified by 2-S-(n-Butylsulfonylamino)-3-[4-(4-(piperidin-4-yl)butyloxy)phenyl]propionic acid; 2-S-(Benzylsulfonylamino)-3-[4-(4-(piperidin-4-yl)butyloxy)phenyl]propionic acid; and 2-S-(2-Phenethylsulfonylamino)-3-[4-(4-(piperidin-4-yl)butyloxy)phenyl]-propionic acid, and pharmaceutically acceptable salts thereof, are significantly more stable on storage when formulated in the presence of a citrate buffer for buffering the composition instead of a phosphate buffer. This finding is surprising because phosphate buffers are commonly used by persons skilled in the area of pharmaceutical formulation.

The citrate buffered formulation of the invention includes an amount of citrate effective to provide a pharmaceutically acceptable pH, e.g. to provide a pH environment of between 5 and 7, preferably between about 5.8 and 6.2, e.g., about 6. In order to provide a pharmaceutically acceptable amount of citrate buffer effective to achieve the desired pH, suitable amounts of sodium citrate and citric acid can be used.

Tonicity adjusting agents, including sodium chloride, are used to adjust tonicity for osmotic pressure and prevent blood cell lysing. These agents minimize pain and thrombophlebitis often experienced by patients receiving intravenous administrations of pharmaceutical compositions. The amount used is that which makes the formulation isotonic with osmotic pressure of the biological system of the patient. Expressed in osmolarity units, the preferred amount of tonicity adjusting agent suitable for the present invention, e.g., sodium chloride, is between about 50–500 milliosmoles, more preferably about 290 milliosmoles. In compositions of the invention, pharmaceutically acceptable osmolarity can be achieved by formulating with an amount of sodium chloride of between about 1.5 and 15 mg/ml, preferably about 9 mg/ml. Such osmolality can also be achieved by using an amount of mannitol of between about 7 and 75 mg/ml, preferably about 50 mg/ml. Other tonicity adjusting agents which can be used to adjust tonicity include, but are not limited to, dextrose and other sugars.

The compositions are not limited to the active ingredient, citrate buffer and tonicity adjusting agent, however, and may also include other pharmaceutically acceptable diluents, excipients or carriers. The formulations are suitable for long-term storage in glass containers commonly used in the pharmaceutical industry, e.g., in concentrated form in standard USP Type I borosilicate glass containers.

In general, the procedure for preparing the compositions of the invention involves combining the various ingredients in a mixing vessel, e.g., at room temperature. The active ingredient (in salt or free base form), citrate buffer sources (e.g., citric acid and sodium citrate), and tonicity adjusting agent, are combined to obtain an active ingredient concentration of between about 0.01 mg/ml and 0.5 mg/ml.

In one procedure for preparing the composition, a substantial portion of the finished product amount of water (e.g., between about 60 and 100%) is introduced into a standard pharmaceutical mixing vessel. An amount of active ingredient suitable for obtaining the desired finished product concentration is dissolved in the water. Amounts of sodium citrate and citric acid sufficient to obtain a finished citrate concentration of between about 2 and 20 mM, are added. A pharmaceutically acceptable amount of tonicity adjusting agent in the isotonic range, is added. Any remaining portion of water is then added to achieve the desired final concentrations of ingredients. The amount of water initially used in preparing the formulation, and the amount of the remaining portion of water added at the end of the procedure, does not affect the properties of the finished product. Such amounts are a matter of choice for the skilled artisan, allowing for pH adjustment during formulation.

Compositions of the invention have been stored at 5, 30, and 40 degrees C. After 18 months, the compositions show no sign of particulate formation as measured using scanning electron microscopy light obstruction analysis described in the USP National Formulary, The United States Pharmacopeial Convention, Inc., (Rockville, Md.) 1994 pp. 1954–1957.

Concentrated formulations of the compositions can be diluted at the time of administration with a suitable diluent to obtain a finished concentration, for example, of about 0.01 mg/ml, which is suitable for transfer to an infusion bag and use by the patient in need of the desired active ingredient.

The term "pharmaceutically acceptable salts" means non-toxic salts of the active ingredients which are generally prepared by reacting the free base with a suitable organic or inorganic acid. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, valerate.

Active ingredients included within the compositions of the present invention are chiral; included within the scope of the present invention are racemic mixtures and separated enantiomers of the general formula. Furthermore, all diastereomers, including E, Z isomers, of the general formula, are included in the present scope. Furthermore, hydrates as well as anhydrous compositions and polymorphs of the general formula are within the present invention.

The term "pharmaceutically effective amount" shall mean that amount of active ingredient that will elicit the biological or medical response of a tissue, system or animal that is being sought by a researcher or clinician.

The term "alkyl" means straight or branched alkane containing 1 to about 10 carbon atoms, e.g., methyl, ethyl, n-propyl, isopropyl, n-butyl, isobutyl, sec-butyl, tert-butyl, pentyl, iso-amyl, hexy, octyl radicals and the like, straight or branched alkene containing 2 to about 10 carbon atoms, e.g., propylenyl, buten-1-yl, isobutenyl, pentenylen-1-yl, 2,2-methylbuten-1-yl, 3-methylbuten-1-yl, hexen-1-yl, hepten-1-yl, and octen-1-yl radicals and the like, or straight or branched alkyne containing 2 to about 10 carbon atoms, e.g., ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

The term "aryl" means a 5- or 6-membered aromatic ring containing 0, 1, or,2 heteroatoms selected from O, N, and S, e.g., phenyl, pyridine, pyrimidine, imidazole, thiophene, oxazole, isoxazole, thiazole, and amino- and halogen-substituted derivatives thereof.

The term "alkyloxy" includes an alkyl portion where alkyl is as defined above, e.g., methyloxy, propyloxy, and butyloxy.

The term "aralkyl" includes phenylalkyl, pyridylalkyl, thienylalkyl, tetrazolealkyl or oxazolealkyl. The $C_{1-10}$ designation refers to the alkyl component of the aralkyl unit. Examples of arylalkyl include benzyl, fluorobenzyl, chlorobenzyl, phenylethyl, phenylpropyl, fluorophenylethyl, chlorophenylethyl, thienylmethyl, thienylethyl, and thienylpropyl. Examples of alkylaryl include toluene, ethylbenzene, propylbenzene, methylpyridine, ethylpyridine, propylpyridine, butylpyridine, butenylpyridine, and pentenylpyridine.

Compositions of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. Compositions of this invention may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between gp IIb/IIIa on the platelet membranes and fibrinogen adsorbed to the surface of the circuit. (Gluszko et al., Amer. J. Physiol., 252(H), 615–621 (1987)). Platelets released from artificial surfaces show impaired hemostatic function. Compositions of the invention may be administered to prevent adhesion.

Other applications of these compositions include prevention of platelet thrombosis, thromboembolism and reocclusion during and after thrombolytid therapy and prevention of platelet thrombosis, thromboembolism and reocclusion after angioplasty or coronary artery bypass procedures. They may also be used to prevent myocardial infarction.

The dosage regimen utilizing the compositions of the present invention is selected in accordance with a variety of factors including type, species, age, weight, sex and medical condition of the patient; the severity of the condition to be treated; the route of administration; the renal and hepatic function of the patient; and the particular active ingredient or salt thereof employed. An ordinarily skilled physician or veterinarian can readily determine and prescribe the effective amount of the drug required to prevent, counter, or arrest the progress of the condition.

Intravenously, the most preferred doses of active ingredient will range from about 0.01 to about 0.25 µg/kg/minute during a constant rate infusion, e.g., 0.15 µg/kg/minute. In order to administer that amount of active ingredient, a composition of the invention having 0.05 mg/ml of active ingredient should be administered at a rate of between about 0.001 and 0.005 ml/kg/min, e.g., 0.003 ml/kg/min. Compositions of the invention containing higher concentrations of active ingredients should be administered at correspondingly lower rates.

EXAMPLE 1

2-S-(n-Butylsulfonylamino)-3-[4-(4-(piperidin-4-yl) butyloxy)phenyl]propionic acid formulation with citrate buffer A pharmaceutical composition, having 2-S-(n-Butylsulfonylamino)-3-[4-(4-(piperidin-4-yl)butyloxy) phenyl]propionic acid, citrate buffer, and sodium chloride, was prepared at room temperature using 2-S-(n-Butylsulfonylamino)-3-[4-(4-(piperidin-4-yl)butyloxy) phenyl]propionic acid hydrochloride salt, to obtain a free base equivalent concentration of 2-S-(n-Butylsulfonylamino)-3-[4-(4-(piperidin-4-yl)butyloxy) phenyl]propionic acid of 0.25 mg/ml.

800 grams of water was introduced into a standard pharmaceutical mixing vessel. 0.28 grams of 2-S-(n-Butylsulfonylamino)-3-[4-(4-(piperidin-4-yl)butyloxy) phenyl]propionic acid hydrochloride salt was dissolved in the water. 2.7 grams sodium citrate and 0.16 grams citric acid were added to obtain a citrate concentration of 10 mM. 9 grams of sodium chloride was added. 200 grams of water was then added to achieve the desired final concentrations of ingredients. The resulting aqueous formulation had the following concentrations:

| Ingredient | Amount |
| --- | --- |
| 2-S-(n-Butylsulfonylamino)-3-[4-(4-(piperidin-4-yl)butyloxy)phenyl]propionic acid mg/ml | 0.25 |
| citrate buffer | 10 mM |
| sodium chloride | 9 mg/ml |

The finished concentrated formulation was stored in a standard USP Type I borosilicate glass container at 5, 30, and 40 degrees C. After 18 months, the formulation showed no visible particles as measured using scanning electron microscopy light obstruction analysis.

The concentrated formulation was diluted in a 4:1 ratio resulting in a finished concentration of 0.05 mg/ml prior to administration to the patient.

EXAMPLE 2

2-S-(Benzylsulfonylamino)-3-[4-(4-(piperidin-4-yl) butyloxy)phenyl]propionic acid formulation with citrate buffer A pharmaceutical composition having 2-S-(Benzylsulfonylamino)-3-[4-(4-(piperidin-4-yl)butyloxy) phenyl]propionic acid, a citrate buffer, and sodium chloride, was prepared at room temperature using 2-S-(Benzylsulfonylamino)-3-[4-(4-(piperidin-4-yl)butyloxy) phenyl]propionic acid hydrochloride salt, to obtain a free base equivalent concentration of 2-S-(Benzylsulfonylamino)-3-[4-(4-(piperidin-4-yl)butyloxy) phenyl]propionic acid of 0.25 mg/ml.

800 grams of water is introduced into a standard pharmaceutical mixing vessel. 0.28 grams of 2-S-(Benzylsulfonyl-amino)-3-[4-(4-(piperidin-4-yl)butyloxy) phenyl]propionic acid hydrochloride salt is dissolved in the water. 2.7 grams sodium citrate and 0.16 grams citric acid are added to obtain a citrate concentration of 10 mM. 9 grams of sodium chloride is added. 200 grams of water is then added to achieve the desired final concentrations of ingredients. The resulting aqueous formulation have the following concentrations:

| Ingredient | Amount |
| --- | --- |
| 2-S-(Benzylsulfonylamino)-3-[4-(4-(piperidin-4-yl)butyloxy)phenyl]propionic acid mg/ml | 0.25 |
| citrate buffer | 10 mM |
| sodium chloride | 9 mg/ml |

The finished concentrated formulation is stored in a standard USP Type I borosilicate glass container at 5, 30, and 40 degrees C. After 18 months, the formulation shows no visible particles as measured using scanning electron microscopy light obstruction analysis.

The concentrated formulation is diluted in a 4:1 ratio resulting in a finished concentration of 0.05 mg/ml prior to administration to the patient.

EXAMPLE 3

2-S-(n-Butylsulfonylamino)-3-[4-(4-(piperidin-4-yl) butyl-oxy)phenyl]propionic acid formulation with citrate buffer The procedure in Example 1 is followed except that 0.05 grams instead of 0.28 grams of 2-S-(n-Butylsulfonylamino)-3-[4-(4-(piperidin-4-yl)butyloxy)phenyl]propionic acid hydrochloride salt is dissolved in the water.

The finished concentrated formulation is stored in a standard USP Type I borosilicate glass container at 5, 30, and 40 degrees C. After 18 months, the formulation shows no visible particles as measured using scanning electron microscopy light obstruction analysis.

No dilution is required prior to administration to the patient.

EXAMPLE 4

2-S-(n-Butylsulfonylamino)-3-[4-(4-(piperidin-4-yl) butyloxy)phenyl]propionic acid formulation with citrate buffer The procedure in Example 1 is followed except that 0.5 grams instead of 0.28 grams of 2-S-(n-Butylsulfonylamino)-3-[4-(4-(piperidin-4-yl)butyloxy)phenyl]propionic acid hydrochloride salt is dissolved in the water. The finished concentrated formulation is stored in a standard USP Type I borosilicate glass container at 5, 30, and 40 degrees C. No visible particles are observed. Dilution is required prior to administration to the patient.

EXAMPLE 5

2-S-(n-Butylsulfonylamino)-3-[4-(4-(piperidin-4-yl) butyloxy)phenyl]propionic acid formulation with citrate buffer The procedure of Example 1 is followed except that 8 grams dextrose rather than sodium chloride is used as the tonicity adjusting agent. The finished concentrated formulation is stored in a standard USP Type I borosilicate glass container at 5, 30, and 40 degrees C. No visible particles are observed. No dilution is required prior to administration to the patient.

EXAMPLE 6

2-S-(n-Butylsulfonylamino)-3-[4-(4-(piperidin-4-yl)butyloxy)phenyl]propionic acid formulation with citrate buffer The procedure of Example 1 is followed except that 15 grams sodium chloride is used as the tonicity adjusting agent. The finished concentrated formulation is stored in a standard USP Type I borosilicate glass container at 5, 30, and 40 degrees C. No visible particles are observed. No dilution is required prior to administration to the patient.

EXAMPLE 7

2-S-(n-Butylsulfonylamino)-3-[4-(4-(piperidin-4-yl)butyloxy)phenyl]propionic acid formulation with phosphate buffer In order to compare the stability of citrate formulations to phosphate formulations, a phosphate buffered formulation containing 0.5 mg/ml 2-S-(n-Butylsulfonylamino)-3-[4-(4-(piperidin-4-yl)butyloxy)phenyl]propionic acid, phosphate buffer, and sodium chloride was prepared, stored and analyzed for visible particles as measured using scanning electron microscopy light obstruction analysis.

800 grams of water was introduced into a standard pharmaceutical mixing vessel. 0.56 grams of 2-S-(n-Butylsulfonyl-amino)-3-[4-(4-(piperidin-4-yl)butyloxy)phenyl]propionic acid hydrochloride salt was dissolved in the water. 0.4 grams sodium phosphate monobasic and 1.02 grams sodium phosphate dibasic were added to obtain a finished phosphate concentration of 10 mM. 9 grams of sodium chloride was added. 200 grams of water was then added to achieve the desired final concentrations of ingredients.

The resulting aqueous formulation had the following concentrations:

| Ingredient | Amount |
| --- | --- |
| 2-S-(n-Butylsulfonylamino)-3-[4-(4-(piperidin-4-yl)butyloxy)phenyl]propionic acid mg/ml | 0.5 |
| phosphate buffer | 10 mM |
| sodium chloride | 9 mg/ml |

The finished concentrated formulation was stored in a standard USP Type I borosilicate glass container at 5, 30, and 40 degrees C.

Particles having size greater than 50 μm, visible without the assistance of electron microsscopy, were observed in vials stored for 24 months at 30° C. and 40° C.

Particles having size greater than 50 μm, visible without the assistance of electron microsscopy, were also observed in vials stored for 36 months at 30° C. and 40° C.

Particulate formation of particles having sizes >10 μm was measured, using scanning electron microscopy light obstruction analysis, by determining "counts" per 125 ml vial corresponding to formulations stored in vials for 36 months at 5° C., 30° C., and 40° C. A subset of particles having sizes >25 μm was also determined.

| Temp. (° C.) | >10 μm (counts/vial) | >25 μm (counts/vial) |
| --- | --- | --- |
| 5 | 417 | 50 |
| 30 | 283 | 50 |
| 40 | 323083 | 42 |

What is claimed is:

1. An aqueous pharmaceutical composition for intravenous administration to a patient comprising
   a) a compound which is 2-S-(n-Butylsulfonylamino)-3-[4-(4-(piperidin-4-yl)butyloxy)phenyl]propionic acid or a pharmaceutically acceptable salt thereof;
   b) a concentration of a citrate buffer buffer effective to provide a pharmaceutically acceptable pH;
   c) a concentration of a tonicity adjusting agent effective to make the formulation substantially isotonic with the osmotic pressure of the biological system of the patient.

2. A pharmaceutical composition of claim 1, wherein the compound is 2-S-(n-Butylsulfonylamino)-3-[4-(4-(piperidin-4-yl)butyloxy)phenyl]propionic acid, and the concentration of citrate buffer is about 2–20 mM.

3. A composition of claim 2, wherein the concentration of 2-S-(n-Butylsulfonylamino)-3-[4-(4-(piperidin-4-yl)butyloxy)phenyl]propionic acid or a salt thereof is about 0.05 to about 0.25 mg/ml.

4. A composition of claim 2, wherein the concentration of 2-S-(n-Butylsulfonylamino)-3-[4-(4-(piperidin-4-yl)butyloxy)phenyl]propionic acid is about 0.25 mg/ml, the concentration of citrate buffer is about 10 mM, the concentration of tonicity adjusting agent is sufficient to achieve a solution osmolarity of about 290 mOsmol/L, and the pH is about 6.

5. A composition of claim 3, wherein the concentration of 2-S-(n-Butylsulfonylamino)-3-[4-(4-(piperidin-4-yl)butyloxy)phenyl]propionic acid or salt thereof is about 0.05 mg/ml, the concentration of citrate buffer is about 10 mM, the concentration of tonicity adjusting agent is sufficient to achieve a solution osmolarity of about 290 mOsmol/L, and the pH is about 6.

6. A method for inhibiting the aggregation of blood platelets in a mammal, comprising intravenously treating the mammal with a therapeutically effective amount of the composition of claim 2.

7. A method of claim 6 where the mammal is a human.

8. A method for inhibiting the aggregation of blood platelets in a mammal, comprising intravenously treating the mammal with a therapeutically effective amount of the composition of claim 1.

9. A method of claim 8 where the mammal is a human.

10. A composition of claim 1 comprising a concentration of a citrate buffer effective to provide a pH of between about 5 and 7, and a concentration of a tonicity adjusting agent sufficient to achieve a solution osmolarity of between about 50–500 mOsmol/L.

11. A composition of claim 10 comprising about 0.01–0.5 mg/ml of the compound, or a pharmaceutically acceptable salt thereof, about 2–100 mM citrate buffer, and a concentration of a tonicity adjusting agent sufficient to achieve a solution osmolarity of between about 50–500 mOsmol/L.

12. A composition of claim 11 comprising about 2–20 mM citrate buffer, and a concentration of a tonicity adjusting agent sufficient to achieve a solution osmolarity of about 290 mOsmol/L.

13. A composition of claim 1 wherein the compound is 2-S-(n-Butylsulfonylamino)-3-[4-(4-(piperidin-4-yl)butyloxy)phenyl]propionic acid or a salt thereof in a concentration of about 0.25 mg/ml, the concentration of citrate buffer is about 10 mM, the concentration of tonicity adjusting agent is sufficient to achieve a solution osmolality of about 316 mOsmol/kg, and the pH is about 6.

14. A composition of claim 1 wherein the compound is 2-S-(n-Butylsulfonylamino)-3-[4-(4-(piperidin-4-yl)butyloxy)phenyl]propionic acid or a salt thereof in a concentration of about 0.05 mg/ml, the concentration of citrate buffer is about 10 mM, the concentration of osmolality of about 315 mOsmol/kg, and the pH is about 6.

15. A composition prepared by mixing
   a) an amount of 2-S-(n-Butylsulfonylamino)-3-[4-(4-(piperidin-4-yl)butyloxy)phenyl]propionic acid hydrochloride salt sufficient to obtain a final solution 2-S-(n-Butylsulfonylamino)-3-[4-(4-(piperidin-4-yl)butyloxy)phenyl]propionic acid concentration of between 0.01 mg/ml and 0.5 mg/ml;
   b) an amount of sodium citrate and an amount of citric acid sufficient to obtain a final solution pH of between 5 and 7; and
   c) an amount of tonicity adjusting agent sufficient to provide solution osmolarity of between about 50 and 500 mOsmol/L.

16. A composition of claim 15, wherein the amount of 2-S-(n-Butylsulfonylamino)-3-[4-(4-(piperidin-4-yl)butyloxy)phenyl]propionic acid hydrochloride salt is sufficient to obtain a final solution 2-S-(n-Butylsulfonylamino)-3-[4-(4-(piperidin-4-yl)butyloxy)phenyl]propionic acid concentration of between 0.05 mg/ml and 0.25 mg/ml.

17. A composition of claim 15, wherein the amount of sodium citrate and the amount of citric acid is sufficient to obtain a pH of between about 5.8 and 6.2.

18. A composition of claim 15, wherein the amount of tonicity adjusting agent is sufficient to provide solution osmolarity of about 290 mOsmol/L.

19. A composition of claim 15, wherein
   a) the amount of 2-S-(n-Butylsulfonylamino)-3-[4-(4-(piperidin-4-yl)butyloxy)phenyl]propionic acid hydrochloride salt is sufficient to obtain a final solution 2-S-(n-Butylsulfonylamino)-3-[4-(4-(piperidin-4-yl)butyloxy)phenyl}propionic acid concentration of about 0.05 mg/ml;
   b) the amount of sodium citrate and an amount of citric acid is sufficient to obtain a final solution pH of about 6; and
   c) the amount of tonicity adjusting agent is sufficient to provide solution osmolarity of about 290 mOsmol/L.

20. A composition of claim 15, wherein
   a) the amount of 2-S-(n-Butylsulfonylamino)-3-[4-(4-(piperidin-4-yl)butyloxy)phenyl]propionic acid hydrochloride salt is sufficient to obtain a final solution 2-S-(n-Butylsulfonylamino)-3-[4-(4-(piperidin-4-yl)butyloxy)phenyl]propionic acid concentration of about 0.25 mg/ml;
   b) the amount of sodium citrate and an amount of citric acid is sufficient to obtain a final solution pH of about 6; and
   c) the amount of tonicity adjusting agent is sufficient to provide solution osmolarity of about 290 mOsmol/L.

21. A composition prepared by mixing
   a) an amount of 2-S-(n-Butylsulfonylamino)-3-[4-(4-(piperidin-4-yl)butyloxy)phenyl]propionic acid hydrochloride salt is sufficient to obtain a final solution 2-S-(n-Butylsulfonylamino)-3-[4-(4-(piperidin-4-yl)butyloxy)phenyl]propionic acid concentration of about 0.25 mg/ml;
   b) an amount of sodium citrate and an amount of citric acid is sufficient to obtain a final solution pH of about 6; and
   c) an amount of tonicity adjusting agent is sufficient to provide solution osmolality of about 316 mOsmol/kg.

22. A composition prepared by mixing
   a) an amount of 2-S-(n-Butylsulfonylamino)-3-[4-(4-(piperidin-4-yl)butyloxy)phenyl]propionic acid hydrochloride salt is sufficient to obtain a final solution 2-S-(n-Butylsulfonylamino)-3-[4-(4-(piperidin-4-yl)butyloxy)phenyl}propionic acid concentration of about 0.05 mg/ml;
   b) an amount of sodium citrate and an amount of citric acid is sufficient to obtain a final solution pH of about 6; and
   c) an amount of tonicity adjusting agent is sufficient to provide solution osmolality of about 315 mOsmol/kg.

* * * * *